(12) United States Patent
Ekramoddoullah et al.

(10) Patent No.: US 6,306,585 B1
(45) Date of Patent: Oct. 23, 2001

(54) PIN M III GENE IN WHITE PINE

(75) Inventors: Abul K. M. Ekramoddoullah; Douglas W. Taylor; Xueshu Yu; Santosh Misra, all of Victoria (CA)

(73) Assignee: Her Majesty the Queen in right of Canada, as represented by the Minister of Natural Resources, Canadian Forest Service, Ottawa (CA)

( * ) Notice: Subject to any disclaimer, the term of this patent is extended or adjusted under 35 U.S.C. 154(b) by 0 days.

(21) Appl. No.: 08/955,629

(22) Filed: Oct. 22, 1997

(51) Int. Cl.$^7$ ............................. C12Q 1/68; C07H 21/02
(52) U.S. Cl. ................................. 435/6; 536/22.1
(58) Field of Search ................. 435/6; 536/22.1, 536/23.1

(56) References Cited

FOREIGN PATENT DOCUMENTS

9305164-A 6 * 3/1993 (WO).

* cited by examiner

*Primary Examiner*—Eggerton A. Campbell
(74) *Attorney, Agent, or Firm*—George A. Seaby

(57) ABSTRACT

A gene coding for *Pin m* III, which is associated with overwintering and frost hardiness in western white pine, has been cloned and characterized. The gene contains an open reading frame of 486 base pairs, encoding a protein of 161 amino acid residues, with a calculated molecular weight of 18002.30 daltons. The predicted isoelectricl point is 5.534. The gene is transcriptionally regulated with the highest expression in fall and winter months. The protein *Pin m* III is high in infected tissue such as canker. Accordingly, the gene can be used to determine frost hardiness and blister resist fungus susceptibility in conifers.

4 Claims, 7 Drawing Sheets

```
                         SEQUENCE LISTING (1) GENERAL INFORMATION:

(iii) NUMBER OF SEQUENCES: 2

(2) INFORMATION FOR SEQ ID NO: 1:

(i) SEQUENCE CHARACTERISTICS:
        (A) LENGTH: 806 base pairs
        (B) TYPE: nucleic acid
        (C) STRANDEDNESS: single
        (D) TOPOLOGY: linear (ii) MOLECULE TYPE: cDNA AND ITS ENCODED PROTEIN (ix) FEATURE:
        (A) NAME/KEY: open reading frame of Pin m III
        (B) LOCATION: 55....537

(xi) SEQUENCE DESCRIPTION: SEQ ID NO: 1:

CCC ACG CTC CGA TTG AAG AAA TAT AAG TAT TGT GTA GTT GCG              42

AGA GAG TTG AAA ATG GTG TCA GGG ACT TCA TCA ACG GAA GAG              84
                Met Val Ser Gly Thr Ser Ser Thr Glu Glu
```

```
                                5                         10
GTG GTT CAA GTG GAG GCA AGG AGG TTG TGG AAC GCC ACA ACG        126
Val Val Gln Val Glu Ala Arg Arg Leu Trp Asn Ala Thr Thr
                15                        20

AAA GAC AGC CAC AAC TTC TTG CCA AAG GTT TTG CCC GAA GTT        168
Lys Asp Ser His Asn Phe Leu Pro Lys Val Leu Pro Glu Val
 25              30                        35

TTC ACT TCT GTC ACC TTA CTT CAA GGA GAT GGA GGC GTC GGC        210
Phe Thr Ser Val Thr Leu Leu Gln Gly Asp Gly Gly Val Gly
     40                  45                    50

ACC GTC AAG CAG CTC AAC TTC ACC CCT GGT AAG AAG GAT TTC        252
Thr Val Lys Gln Leu Asn Phe Thr Pro Gly Lys Lys Asp Phe
         55                  60                    65

AGC TTC ATC AAG GAG CGA GTG GAT GAA CTT GAC CAG GAG AAT        294
Ser Phe Ile Lys Glu Arg Val Asp Glu Leu Asp Gln Glu Asn
             70                  75                    80

TTC GTG TAT AAG TAT ACA GCG ATC GAA GGA GGA CCG CTT GGG        336
Phe Val Tyr Lys Tyr Thr Ala Ile Glu Gly Gly Pro Leu Gly
                 85                  90

AAA CAA CTG AGC TCT GCG TGC TTT GAG GTG AAA TTG ATT CCT        378
Lys Gln Leu Ser Ser Ala Cys Phe Glu Val Lys Leu Ile Pro
 95              100                       105

AGG AAA GAA GGG GGA TGC GTA GCG AGG TGG ACC TGT AAC TAC        420
Arg Lys Glu Gly Gly Cys Val Ala Arg Trp Thr Cys Asn Tyr
     110                 115                       120

GAA ACT CTT CCT GGT GTT CAA CCT GAC GAA GGA AAA CTA AAA        462
Glu Thr Leu Pro Gly Val Gln Pro Asp Glu Gly Lys Leu Lys
         125                 130                       135

GAG ATA AAG GAA GAT AGC TTT GGC ATG TTG AAG AAA GTG GAG        504
Glu Ile Lys Glu Asp Ser Phe Gly Met Leu Lys Lys Val Glu
             140                 145                   150

CAG TAT CTC CTC TCC AAT CCC AAC TTA TAC TGC TAG ATA TGT        546
Gln Tyr Leu Leu Ser Asn Pro Asn Leu Tyr Cys
                 155                 160

TTACCTACGC ATAAATAGTG TAGAGCGCGC GCTCACCGTG CAAAATAAAG         596

GAGAGTCACG ATATGACTTC CTCCCATCGT CATTGTCGTT TATGGGCTGT         646

AGGATGCCTT TGTTATGTGT GCGCCTGCGA TCGTATCTTT ATCGTTGCGT         696

GATTATGTGT AGTTCCGTGA ATTCAAATCA ATGTCAACGT TCGTTCAGTA         746

TTGTGTGTTC AGAGCAAAAA AAAAAAAAAA AAAAAAAAAA AAAAAAAAAA         796

AAAAAAAAAA                                                    806

(2) INFORMATION FOR SEQ ID NO: 2:

(i) SEQUENCE CHARACTERISTICS:
        (A) LENGTH: 161 amino acids
        (B) TYPE: amino acid
        (C) STRANDEDNESS: single
        (D) TOPOLOGY: linear (xi) SEQUENCE DESCRIPTION: SEQ ID NO: 2:

Met Val Ser Gly Thr Ser Ser Thr Glu Glu Val Val Gln Val Glu Ala
                 5                  10                      15

Arg Arg Leu Trp Asn Ala Thr Thr Lys Asp Ser His Asn Phe Leu Pro
                 20                  25                      30

Lys Val Leu Pro Glu Val Phe Thr Ser Val Thr Leu Leu Gln Gly Asp
         35                  40                      45

Gly Gly Val Gly Thr Val Lys Gln Leu Asn Phe Thr Pro Gly Lys Lys
```

-continued

```
                50                     55                      60
Asp Phe Ser Phe Ile Lys Glu Arg Val Asp Glu Leu Asp Gln Glu Asn
65                  70                  75                      80

Phe Val Tyr Lys Tyr Thr Ala Ile Glu Gly Gly Pro Leu Gly Lys Gln
                85                  90                  95

Leu Ser Ser Ala Cys Phe Glu Val Lys Leu Ile Pro Arg Lys Glu Gly
            100                 105                 110

Gly Cys Val Ala Arg Trp Thr Cys Asn Tyr Glu Thr Leu Pro Gly Val
        115                 120                 125

Gln Pro Asp Glu Gly Lys Leu Lys Glu Ile Lys Glu Asp Ser Phe Gly
    130                 135                 140

Met Leu Lys Lys Val Glu Gln Tyr Leu Leu Ser Asn Pro Asn Leu Tyr
145                 150                 155                 160

Cys
```

PIN M III GENE IN WHITE PINE

BACKGROUND OF THE INVENTION

1. Field of the Invention

This invention relates to a gene coding for *Pin m* III which is associated with overwintering and frost hardiness of western white pine.

The invention also relates to a method of determining the frost hardiness of a conifer seedling, and to a method for determining the susceptibility of conifers to blister rust fungus.

2. Description of the Prior Art

The following disclosure refers to a plurality of literature references. The references are listed numerically at the end of this disclosure White pine blister rust is a disease of five-needle pines, e.g. western white pine (*Pinus monticola* D. Don), eastern white pine (*Pinus strobes* L.) and sugar pine (*Pinus lambertiana* Dougl.), caused by the blister rust fungus, *Cronartium ribicola* Fisch. The fungus has five different spore stages on two unrelated hosts, white pines and Ribes species. The basidiospores are produced on Ribes in the fall and transported by wind to pine foliage, where they germinate and infect the needle via stomata and produce infection spot. Hyphae grow down the needle into the bark, causing a perennial canker which eventually kills the tree. Although some large and older trees can survive, infected younger trees almost inevitably die. We have been studying proteins involved in this host-pathogen interaction. (e.g. Ekramoddoullah and Hunt, 1993, Ref. 10). During this investigation it was observed that environmental factors also contributed to the changes in the synthesis of proteins. Plants presumably respond to signals generated by environmental stresses, e.g. low and high temperature, photoperiod, drought, salinity and are capable of responding to a varying degree to the stresses (Bohnert et al., 1995, Ref. 3). Plants also are continually exposed to numerous microorganisms but are susceptible only to a few of them. In response to both abiotic and biotic stresses, induction of several proteins in plants have been identified (Heikila et al., 1984, Ref. 16; Ort et al., 1989, Ref. 32; Hightower, 1991, Ref. 17; Stintzi et al., 1993, Ref. 41; Ekramoddoullah et al., 1995, Ref. 12; Sabehat et al., 1996, Ref. 37; Mauch et al. 1988, Ref. 28). Although functions for many of these proteins have not yet been assigned, accumulation of a group of proteins termed "pathogenesis-related" proteins (van Loon, 1985, Ref. 48; Linthorst, 1991, Ref. 25) is considered an important feature of plant defence response upon infection. Some of these proteins could be induced by either abiotic or biotic stress. For example, a protein osmotin that accumulates during adaptation of tobacco cells to osmotic stress could be induced in tobacco leaves infected with tobacco mosaic virus (Stintzi et al., 1991, Ref. 40). Genes encoding vegetative storage proteins were expressed following wounding and water deficit (Mason et al., 1991, Ref. 27). A major protein, sporamin of potato tuberous roots (Maeshima et al., 1985, Ref. 26), which is developmentally regulated, could be induced in petioles by treatment with fungal elicitors, polygalacturonic acid and chitosan (Ohto et al., 1992, Ref. 31). A family of wound induced genes in Populus shares common features with genes encoding vegetative storage proteins (Davis et al., 1993, Ref. 7) that also accumulate seasonally in poplar bark tissues (Clausen and Apel, 1991, Ref. 5)). A group of antifreeze like proteins in rye grass was shown to have amino acid sequence homology with pathogenesis-related proteins (Hon et al., 1995, Ref. 18).

Recently, a sugar pine protein *Pin l* I was detected in the foliage in increasing amounts in the fall (Ekramoddoullah et al. 1995, Ref. 12). The homologue of this fall protein, named as *Pin m* III, was also identified in western white pine foliage. An 89% homology of the N-terminal amino acid sequence of *Pin m* III was found with *Pin l* I (Ekramoddoullah and Taylor, 1996, Ref. 13). The quantity of *Pin m* III in western white pine seedlings was shown to be seasonally regulated; increasing as fall progressed to a maximum in the winter months, and reducing to lowest levels in the summer months (Ekramoddoullah et al. 1995, Ref. 12). *Pin m* III has also been shown to be associated with frost hardiness of western white pine.

SUMMARY OF THE INVENTION

In order to investigate the potential anti-freeze property of Pin m III, the present inventors undertook the molecular cloning and characterization of the gene encoding *Pin m* III, which is one of the objects of this invention. An expression cDNA library from poly(A)+mRNA of pine needles was generated. The gene encoding *Pin m* III was cloned by antibody screening. BLAST search and subsequent sequence comparisons indicated *Pin m* III is a member of intracellular pathogenesis-related protein. This disclosure describes the complete sequence of the cDNA encoding *Pin m* III from western white pine, its phylogenetic relationship to other pathogenesis-related proteins, and analysis of its temporal and spatial expression. Furthermore, data are provided to show that *Pin m* III is also induced by the white pine blister rust fungus.

Accordingly, another object of the invention is to provide methods for determining frost hardiness and blister rust fungus susceptibility in a conifer by detecting the amount of the protein *Pin m* III in the conifer.

Thus according to one aspect, the invention provides a nucleic acid sequence encoding the protein *Pin m* III having the amino acid sequence of SEQ ID NO: 1.

DETAILED DESCRIPTION OF THE INVENTION MATERIAL AND METHODS

Mature Western White Pine

Figure 1:
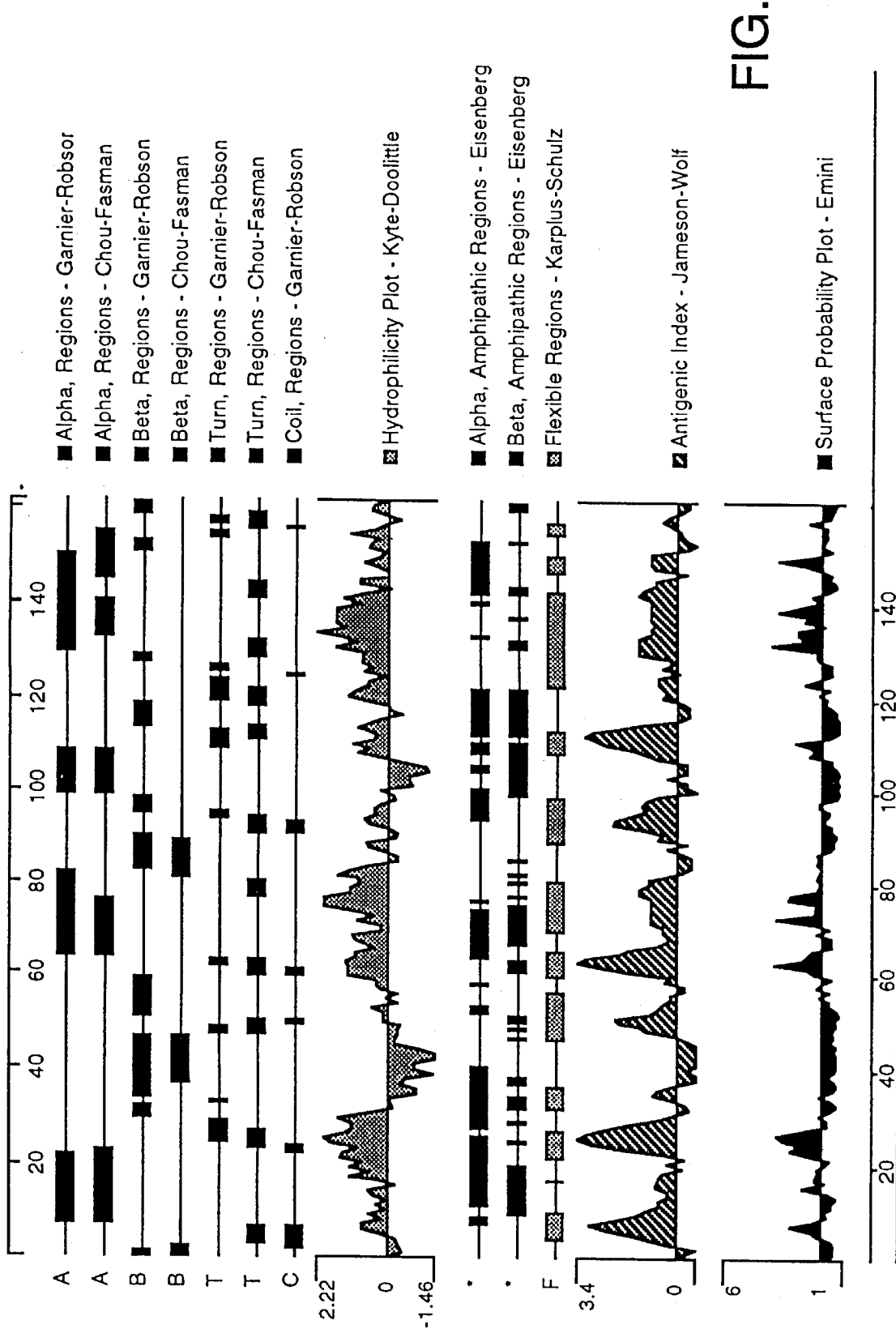
FIG. 1 shows the results of protein sequence analysis of the deduced amino acid sequence of *Pin m* III.

Bark samples (all tissues outside the xylem, including epidermis, periderm, and phloem) were collected from both resistant and susceptible clones grown at Plantation 4/Plot B [Hunt et al. 1987, Ref. 19] located at Lens Creek, Vancouver Island, British Columbia. Selection for resistance (clones G-8, G161 and B643) was based upon so-called 'mature resistance'. Such clones were difficult to infect in a diseased garden; i.e., growing with *C. ribicola* infected Ribes ssp (Porter, 1960, Ref. 34), and ramets have maintained high level of field resistance displaying phenotypic resistance (Hunt and Meagher 1989, Ref. 21). Sampled ramets lack cankers. Similarly tested susceptible clones (G27 and 6149) were also sampled and sampled ramets had four or more cankers. Ramets were 31–33 years-old in 1991. Along with the clonal samples three 'natural' trees were sampled as follows: "resistant" NO-7 (no canker and 7-year old), and susceptible N6-23 (6 cankers and 23 year-old) and N2-15 (2 cankers, 15 year old). All samples were taken from healthy trunk bark in April 1991, October 1993, February 1994 and May 1994.

Western White Pine Seedlings

Two-year old white pine seedlings, were inoculated in August 1992, by suspending Ribes leaves over seedlings (Hunt, 1988, Ref. 20) with a composite inoculum from six coastal British Columbia sources of the blister rust fungus. The seedlings were grown under natural day length and temperature conditions outdoors at Lake Cowichan Research Station (Vancouver Island). The following winter, the seedlings were transferred from styrofoam blocks to either one gallon pots (resistant) or to beds (susceptible). Both susceptible (20 cankered individuals) and resistant (23 individuals displaying slow canker growth; see Hunt 1997, Ref. 22) seedlings were from eight families undergoing screening for blister rust resistance for coastal British Columbia (Meagher et al.1995, Ref. 29). Samples of bark, twig and foliage of these seedlings were collected in July 1995.

Protein Extraction

Proteins were extracted as described by Ekramoddoullah (1991, 1993, Refs. 8 and 9) with minor modifications. Samples of foliage, bark and twig were lyophilized and ground to powder in liquid nitrogen with a mortar and pestle, after which 50 mg of powder was extracted with 0.7 mL of extraction solution (ES) (4% SDS, 5% sucrose, 5% mercaptoethanol) for 10 min at room temperature with gentle stirring. The extract was centrifuged at 10,000 g for 15 min, and the clear supernatant was heated to 100° C. for 3 min and then cooled to room temperature. Proteins were precipitated by adding cold (−20° C.) acetone (8× volume of the supernatant); precipitation was allowed to continue for 1 h, (at −20° C.) after which the sample was centrifuged at 10,000 g. The pellet was resuspended in 0.2 mL of ES, centrifuged at 10,000 g for 15 min, and the protein content of the supernant was determined (Ekramoddoullah and Davidson 1995, Ref. 11) using bovine serum albumin as a standard. Briefly, the protein solution and standard were spotted on a polyvinylidene difluoride membrane IMMOBILON-PT™, available from Millipore Canada Ltd., Toronto, Canada. The membrane was stained with 0.1% Coomassie blue R-250 (Bio-Rad Laboratories, Richmond, Calif., USA) in 50% methanol for 8 min, and then destained in 50% methanol:10% acetic acid for 8 min at room temperature. The membrane was then rinsed with water for 10 min and scanned using a laser scanner (Molecular Dynamics, model 110A, Sunnyvale, Calif., USA) interfaced with a workstation (SPARK 1™, Sun Microsystems of Canada Inc. Vancouver, B.C., Canada) and PDI (Protein+ DNA imageWare systems, Huntington Station, N.Y., USA) for membrane blot processing with the software program ONED™. Scanning, detection and quantification were performed according to the PDI instruction manual.

Quantification of Pin m III by Western Immunoblot

SDS-PAGE was carried out in a protein slab cell apparatus (Bio-Rad) utilizing 0.75-mm thick 12% gel and the Laemmli buffer system (Laemmli 1970, Ref. 23). A sample volume of 25 $\mu$L (containing 5–20 $\mu$g protein) was applied in each well. Proteins separated by SDS-PAGE were electrophoretically transferred (Towbin et al. 1979, Ref. 44) from the gel onto IMMOBILON-P membrane. Following transfer of the separated proteins, the membrane was probed with antibody. The scanning of immunoblots and the preparation of the antibody was described elsewhere (Ekramoddoullah et al. 1995, Ref. 12). The antibody was prepared against a synthetic peptide of 17 amino acid residue of a sugar pine protein Pin l I, but reacts to Pin m III. A sample containing sufficient amount of Pin m III (as determined previously by Western immunoblot) was used as a reference standard to quantify this protein in all samples involving several Western immunoblots. The levels of Pin m III was normalized with respect to this reference standard and expressed as optical density (OD) unit.

Statistical Analysis

Data were analyzed by Student-t and Kruskal-Wallis tests using SAS program (SAS Institute Inc. 1989, Ref. 36).

Plant Material Collection and Treatment for RNA Preparation

The western white pine needles from one year old seedlings were collected in the winter of 1994 and stored at −80° C. The foliage samples of seedlots 2881, 2888 and 3159 for total RNA extractions were the same samples used in the protein analysis as previously described (Ekramoddoullah et al. 1995, Ref. 12). Needle samples used for the expression cDNA library were collected in January, 1996 from a mature western white pine tree growing at the campus of University of Victoria (Victoria, BC, Canada). To analyze tissue specific expression samples from one year old western white pine seedlings (seedlot 3144) were collected in September, 1996 from the shelter house at the Pacific Forestry Centre (Victoria, BC, Canada), frozen in liquid nitrogen and then lyophilized. Current year needles and one year old needles, their corresponding twigs and the roots from the seedling were collected in September 1996 and used in the extraction of total RNA and protein. Sugar pine (Pinus lambertiana) needles (pooled healthy needles alone; pooled infected spots, i.e.+lesions; pooled remainings of infected needles without lesions) from resistant tree (R4) or susceptible tree, (S4) were collected in September 1996 from the shelter house at the Pacific Forestry Centre and treated the same as the one-year-old western white pine seedling. Sugar pine trees were seven years old which were inoculated with the blister fungus in September, 1995.

RNA Extraction

For the cDNA library construction, total RNA was extracted from 10 g western white pine needles collected in January 1996 from the campus of the University of Victoria by the method of Schultz et al. (1994, Ref. 39). The needles were ground to a fine powder in liquid nitrogen with a mortar and pestle. The powder was then transferred to cooled centrifugation tubes, extraction buffer added, and further homogenized in the polytron. The RNA was extracted as described (Schultz et al 1994, Ref. 39). Poly (A)+RNA was isolated by the mRNA Purification Kit from Pharmacia Biotech. For northern blot analysis, total RNA was extracted based on the method of Wang and Vodkin (1994, Ref. 50) with modification. The mRNA concentration was determined spectrophotometrically and also by agarose gel electrophoresis.

Construction of Expression cDNA Library and Antibody Screening of the Library

An expression cDNA library was constructed in $\gamma$t22A from poly(A)+RNA of western white pine needles according to the manufacture's protocol (GibcoBRL, Gaithersburg, Md., U.S.A.). The library was screened with anti -Pin l I antibody. Three initial positive plaques were identified and one was purified through three rounds of screening. The cDNA insert was subcloned into pBluescript KS+ (Stratagene, La Jolla, Calif., U.S.A.).

Northern Blot Analysis

In northern blot analysis, 20 $\mu$g total RNA per lane was electrophoretically separated on 1.2% agarose gels containing 2.2M formaldehyde (Sambrook et al., 1989, Ref. 38), photographed, and transferred to Zeta-Probe GT membranes according to the manufacturers instructions (BIO-Rad, Mississauga, Ontario, Canada). The Pin m III cDNA insert and the genomic DNA 18S ribosomal insert were labeled by random priming with [$\alpha$-$^{32}$P]dCTP and hybridized according to the maunufacturer (Gibco-BRL). The membranes were washed under high stringency also according to the manufacturer (BIO-RAD). Membranes were exposed to BioMax film (Kodak, Rochester, N.Y.) for 3.5 hours for 18S rRNA gene probe, for 3–7 days for Pin m III probe with intensifying screens at −80° C. Northern blot analysis was repeated three times for the seasonal expression analysis and repeated twice for the analysis of tissue specificity and for the infected foliage.

Genomic DNA Extraction and Southern Analysis

Genomic DNA was extracted by the CTAB method. 30 μg aliquots of DNA was digested with restriction enzymes overnight at 37° C., electrophoresed through 0.8% agarose gels and blotted onto Zeta-Probe GT membranes. The *Pin m* III cDNA insert (EcoR I fragment) was labeled, hybridized and washed as in Northern blot analysis. Southern analysis was repeated three times.

DNA Sequencing

The Lambda DNA was purified by the QIAGEN Lambda Maxi Kit (QIAGEN GmbH, Hilden, Germany). The inserts from the γgt22A vector was purified by fractionating the digestion mixture on 1% agrose gel. The insert was then purified by QIAquick Gel Extraction Kit (QIAGEN GmbH, Hilden, Germany). The cDNA insert was subcloned into pBluescript KS+ vector (Stratagene, La Jolla, Calif.). Inserts were sequenced on both strands by the dideoxy method (Sequenase Version 2.0, US Biochemical, Cleveland, Ohio, USA) with T3 and T7 primers and other internal primers based on derived sequences and synthesized using the Applied Biosystems PCR-Mate DNA Synthesizer (Applied Biosystems, Inc., Foster City, Calif., U.S.A.).

Immunoscreening of cDNA Library

Anti -*Pin l* I antibody (Ekramoddoullah et al. 1995, Ref. 12) was used in the immunoscreening of the expression cDNA library. Immunoscreening was conducted following the Stratagene's picoBlueTM immunoscreening instruction manual with some modification. Blocking agents TTBS, gelatin, skim milk and BSA were tested for the antibody screening. Best results were obtained using 5% skim milk powder (5% w/v in TBS) overnight. Western immunoblot analysis was done as described above.

Results

Construction of cDNA Library

Total RNA purified by the method of Wang & Vodkin (1994, Ref. 50) was pooled and subjected to oligo-dT column purification for poly(A)+mRNA. The purified poly(A)+mRNA had 260/280 OD ratio of 1.40 to 1.63. Subsequently, these poly(A)+mRNA were used for the cDNA synthesis and cDNA library construction of five libraries according to the instruction manual of Stratagene. Generated libraries were low in total independent plaques which indicated that RNA was perhaps contaminated and inhibited the efficiency of the cDNA library construction. Finally, the protocol described by Schultz et al. (1994, Ref. 39) was adopted for extraction of total RNA from winter needles. This method gave a lower yield but much cleaner total RNA with 260/280 OD ratio of 1.88 to 2.0. The purified poly(A)+mRNA had 260/280 OD ratio of 1.70 to 1.81. UV scanning confirmed the existence of the 260 nm nucleic acid peak. By combining the Gibco-BRL size fractionation column (from Gibco-BRL SuperScript lambda system) with the Stratagene cDNA synthesizing kit (Stratagene UniZAP XR system), we made an excellent cDNA library using Stratagene's expression vector UniZAP XR. A total of $1 \times 10^6$ independent plaque forming units (pfu) were obtained in the cDNA library.

Cloning and Characterization of *Pin m* III cDNA

Immunoscreening identified three positive clones in the first round. The second and third round immunoscreening of one of the three clones confirmed a specific signal. After three rounds of consecutive screening of the gt22A western white pine needle cDNA expression library with anti-*Pin l* I antibody, the sequence of a cDNA encoding *Pin m* III was obtained. The cDNA *Pin m* III sequence (SEQ ID No: 1) contained 806 bp, a 5' untranslated region of 54-bp followed by an open reading frame of 486-bp *Pin m* III and followed by a 286-bp 3' untranslated region including the poly(A) tail. The deduced open reading frame codes for 161 amino acids. The predicted molecular weight of *Pin m* III is 18002.30 Da. In the 3' noncoding region, a putative polyadenylation signal (AATAAA) was located at position 590. The poly(A) tail was located 221 nucleotides downstream from the TAG translation termination codon. The deduced amino acid sequence of the *Pin m* III had an overall excess of two strongly acidic (−) residues (D,E) in relation to strongly basic (+) amino acids (K,R) (22 acidic versus 20 basic amino acids). It had 50 hydrophobic amino acids (A,I,L,F,W,V) and 44 polar amino acids (N,C,Q,S,T,Y). The predicted isoelectric Point is 5.534. At pH 7.0 the charge is −2.024 . The complete amino acid sequence of *Pin m* III was derived on the basis of the nucleotide sequence of a cDNA clone obtained from the western white pine winter needle mRNA and confirmed by the partial N-terminal protein sequence of *Pin m* III. Protein sequence analysis revealed the presence of α, β, and coil structures (FIG. 1). More importantly, *Pin m* III is very hydrophilic (FIG. 1)—a desirable characteristic of anti-freeze proteins.

*Pin m* III is Similar to Pathogenesis-Related (PR) Proteins

Figure 2:
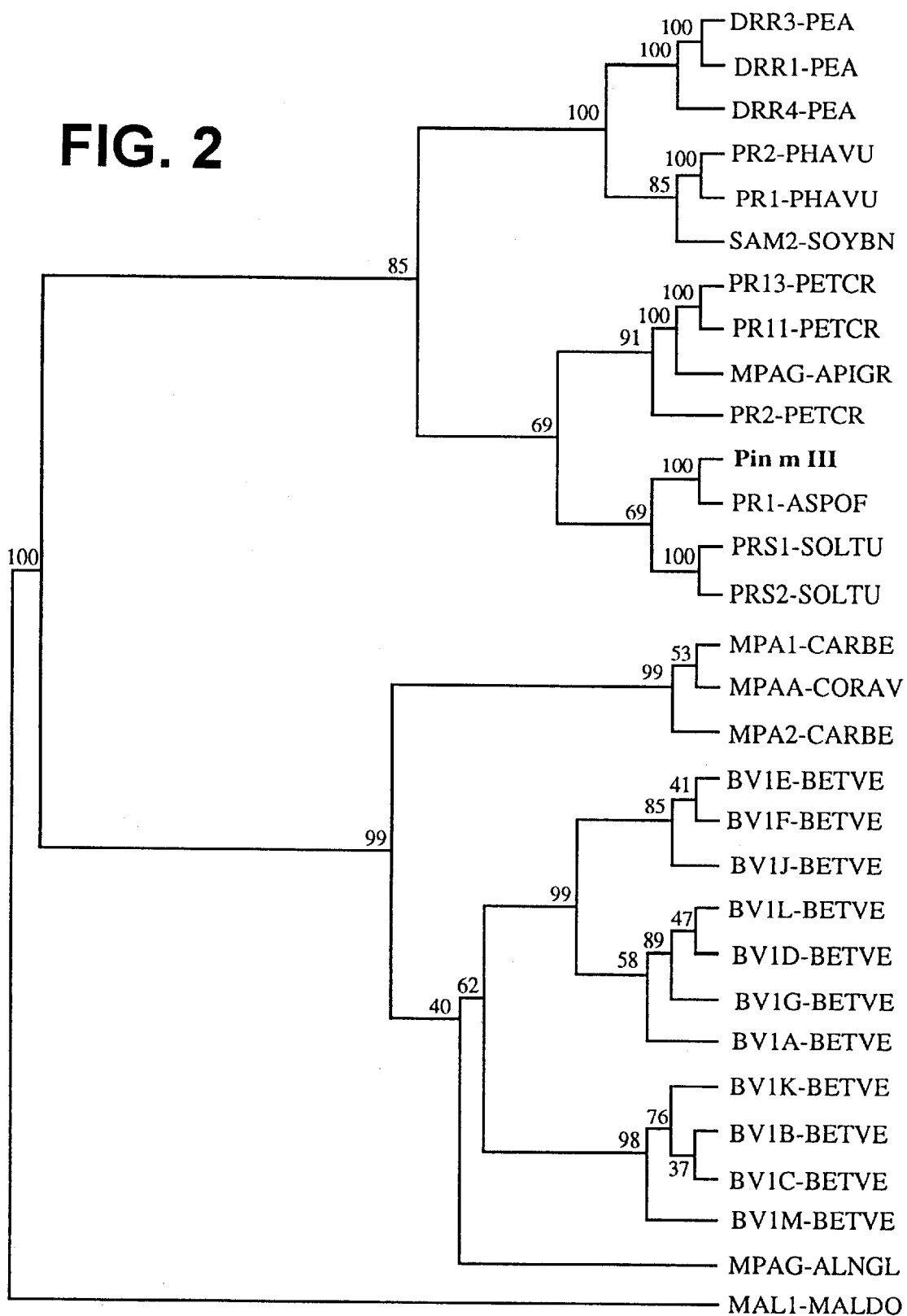
FIG. 2 shows the phylogenetic tree of thirty representative members from the intracellular PR protein family. The consensus phylogenetic tree was constructed using the PHYLIP package (Felsenstein, 1989, Ref. 14) based on multiple sequence alignment using CLUSTAL W 1.6 (Thompson et al, 1994, Ref. 43). The numbers at branches are bootstrap values out of 100 (the number of times the group consisting of the species occurred among the trees, out of 100 trees). The following sequences were used to construct the phylogenetic tree: BV1A__BETVE (major pollen allergen *BET V* I-A from white birch, *Betula verrucosa*, SWISS-PROT: P15494), BV1F__BETVE (major pollen allergen *BET V* I-F/I, SWISS-PROT: P43179), BV1M__BETVE (major pollen allergen *BET V* I-M/N, SWISS-PROT: P43186), BV1B__BETVE (major pollen allergen *BET V* I-B, SWISS-PROT: P45431), BV1C__BETVE (major pollen allergen *BET V* I-C, SWISS-PROT: P43176), BV1D__BETVE (major pollen allergen *BET V* I-D/H, SWISS-PROT: P43177), BV1E__BETVE (major pollen allergen *BET V* I-E, SWISS-PROT: P43178), BV1G__BETVE (major pollen allergen *BET V* I-G, SWISS-PROT: P43180), BV1J__BETVE (major pollen allergen *BET V* I-J, SWISS-PROT: P43183), BV1K__BETVE (major pollen allergen *BET V* I-K, SWISS PROT: P43184), BV1L__BETVE (major pollen allergen *BET V* I-L, SWISS-PROT: P43185), DRR1__PEA (disease resistance response protein PI176 from garden pea, *Pisum sativum*, SWISS PROT: P13239), DRR3_PEA (disease resistance response protein PI49, SWISS-PROT: P14710), DRR4_PEA (disease resistance response protein DRRG49-C, SWISS-PROT: P27047), MAL1_MALDO (major allergen *MAL D* I from apple, *Malus domestica*, SWISS-PROT: P43211), MPA1_CARBE n(major pollen allergen *CAR B* I, isoforms 1A and 1B from hornbeam, *Carpinus betulus*, SWISS-PROT: P38949), MPA2_CARBE (major pollen allergen *CAR B* I, isoform 2, SWISS-PROT: P38950), MPAA_CORAV (major pollen allergen *COR A* I, ISO-FORMS 5, 6, 11 and 16 from European hazel, *Corylus avellana*, SWISS-PROT: Q08407), MPAG_ALNGL (major pollen allergen *ALN G* I alder, *Alnus glutinosa*, SWISS-PROT: P38948), MPAG_APIGR (major allergen *API G* I (*API G* 1) from celery, *Apium graveolens*, SWISS-PROT: P49372), PR11_PETCR (pathogenesis-related protein A (PR1-1) from parsley, *Petroselinum crispum*, SWISS-PROT: P19417), PR13_PETCR (pathogenesis-related protein B (PR1-3), SWISS-PROT: P19418), PR2_PETCR (pathogenesis-related protein 2, SWISS-PROT: P27538), PR1_ASPOF (pathogenesis-related protein 1 (AOPR1) from garden asparagus, *Asparagus officinalis*, SWISS PROT: Q05736), PR1_PHAVU (pathogenesis-related protein 1 (PVPR1) from bean, *Phaseolus vulgaris*, SWISS-PROT: P25985), PR2_PHAVU (pathogenesis-related protein 2 (PVPR2), SWISS-PROT: P25986), PRS1_SOLTU (pathogenesis-related protein *STH*-21 from potato, *Solanum tuberosum*, SWISS-PROT: P17641), PRS2_SOLTU (pathogenesis-related protein *STH* 2, SWISS-PROT: P17642), SAM2_SOYBN (stress-induced protein SAM22 from soybean, *Glycine max*, SWISS-PROT: P26987).

The BLAST search (Altschul et al., 1990, Ref. 1) of the nucleotide and protein databases revealed similarities between the sequences of *Pin m* III and a group of intracellular pathogenesis-related (PR) proteins and a group of major tree pollen allergens (FIG. 2). *Pin m* III shares from 22 to 36.7 percent similarity (according to DNASTAR, using Clustal method with PAM250 residue weight table) with the representative PR and allergen family members from angiosperm plants. The highest similarity is with the PR1 from asparagus (36.7%). The IPRs form a phylogenetic subgroup (except the celery allergen) while the allergens form a separate subgroup (FIG. 2).

A Small Multigene Family Codes for *Pin m* III in Western White Pine

Figure 3:
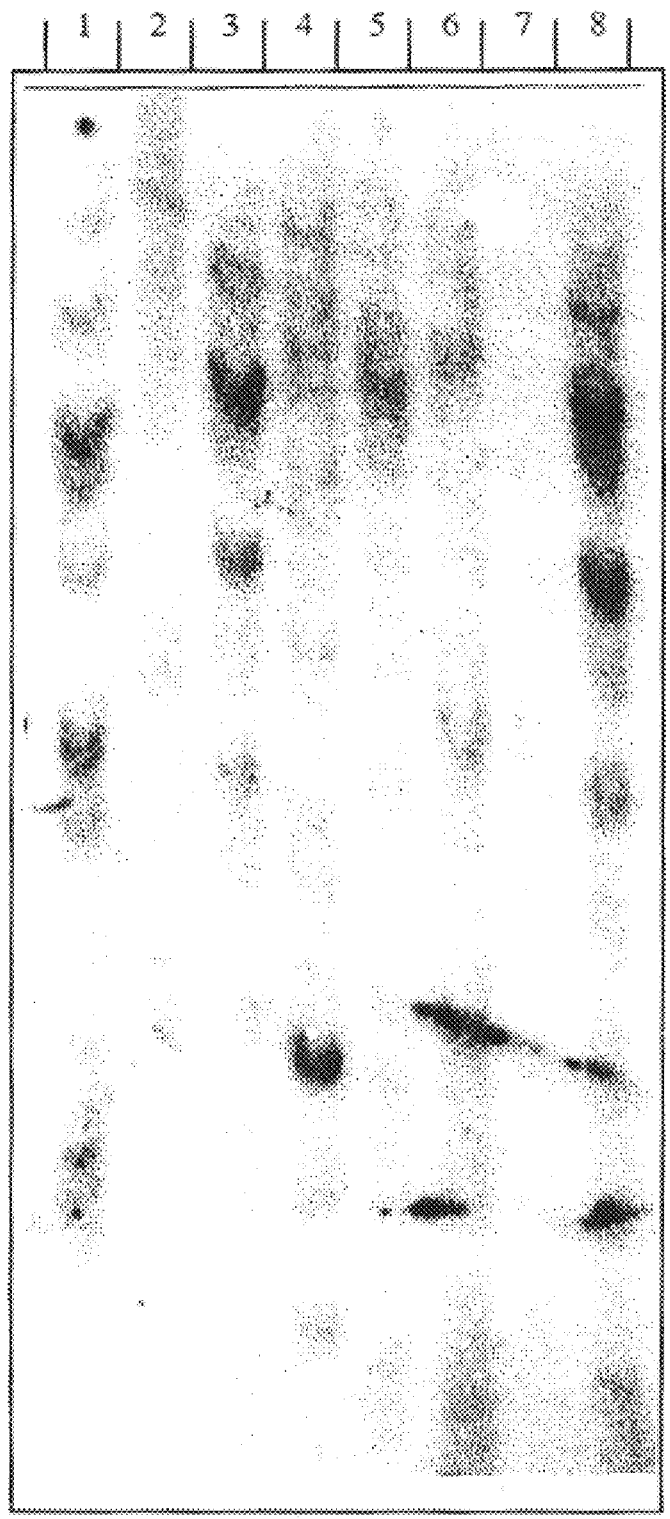
FIG. 3 shows the results of Southern blot analysis of genomic DNA of western white pine and related species. Thirty $\mu$g of genomic DNA was used in each overnight digestion. Lanes 1–4: genomic DNA of western white pine digested with Xba I (lane 1), Bam HI (lane 2); Hind III (lanes 3 and 8), Eco RI (lane 4); genomic DNA of eastern white pine digested with Hind III (lane 5); ponderosa pine genomic DNA digested with Hind III (lane 6); and tobacco genomic DNA digested with Hind III (lane 7)

FIG. 3 shows the Southern analysis of genomic DNA of western white pine, eastern white pine and ponderosa pine (*Pinus ponderosa* Dougl.) that were digested with four different restriction enzymes: Xba I, Bam HI, Hind III, Eco RI. For western white pine, the Xba I digestion gives at least seven different bands, while Eco RI and Hind III digestion showed at least four bands. Bam HI digestion also gives multiple bands, at least four distinct bands (on another repeated blot). These results would indicate that *Pin m* III in western white pine is encoded by a small polymorphic family of 4 to 8 genes and the western white pine genome has a small gene family encoding *Pin m* III. Eastern white pine (*Pinus strobus* L.) genome digested with Hind III or Eco RI (data not shown) gave a similar banding pattern as that of western white pine. On the other hand, genomic DNA of ponderosa pine had multiple bands differing in sizes as compared to that of western white pine. Tobacco (*Nicotiana tabacum* L.) genomic DNA did not cross-hybridize with *Pin m* III probe (lane 7, FIG. 3) suggesting the similarity in PR gene family between conifers and dicotyledonous plants is low.

Seasonal Regulation of the *Pin m* III Transcript

Figure 4:
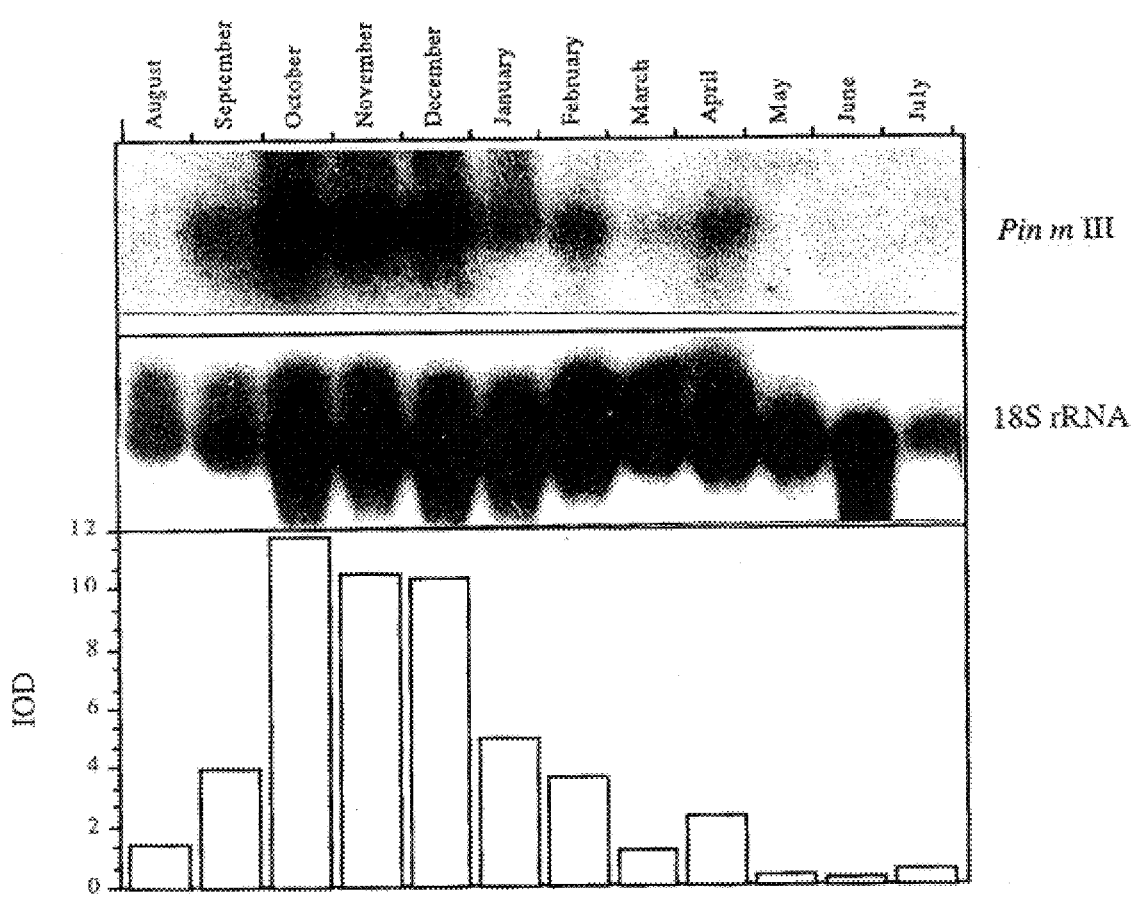
FIG. 4 shows RNA gel blot analysis of seasonal expression of *Pin m* III transcripts in the foliage of one year old western white pine seedlings. Total RNA was isolated, electrophoresed, and transferred to membranes as described hereinafter in "Materials and Methods". *Pin m* III transcript of ca. 0.9 kb was detected using a $^{32}$P radiolabeled probe of the full length *Pin m* III insert. The membranes were exposed for one week. Samples were collected from seed lot 2888. Lane 1, August, 1992; lane 2, September 1992; lane 3, October 1992; lane 4, November 1992; lane 5, December 1992; lane 6, January 193; lane 7, February 1993; lane 8, March 1993; lane 9, April 1993; lane 10, May 1993; lane 11, June 1993; lane 12, July 1993.
Figure 5:
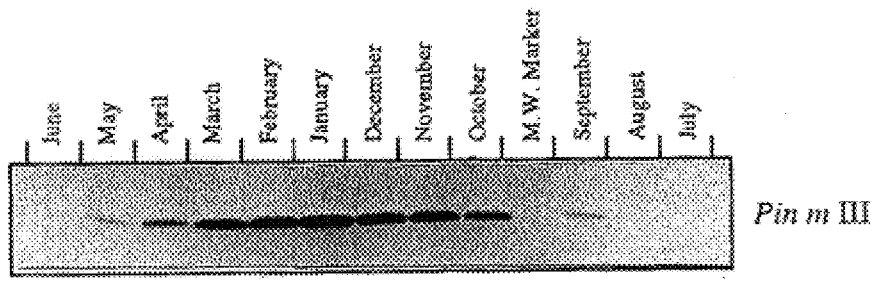
FIG. 5 shows Western immunoblot analysis of seedlot 2881 foliage proteins showing the seasonal variation of the *Pin m* III content. Five $\mu$g of total protein was loaded in each lane. The blot was probed with anti-*Pin l* I antibody. Lane 1, June 1993 foliage sample; lane 2, May, 1993; lane 3, April 1993; lane 4, March 1993 foliage sample; lane 5, February 1993; lane 6, January 1993; lane 7, December 1992; lane 8, November 1992; lane 9, October 1992; lane 10, MW marker; lane 11, September 1992; lane 12, August 1992 and lane 13, July 1992.

Northern analysis showed that the highest message was in October (FIG. 4) while Western immunoblot analysis showed that the highest amount of the *Pin m* III is in January (FIG. 5). The trend of the mRNA is the same among three repeated Northern analysis.

Tissue Specific Expression of *Pin m* III

Figure 6:
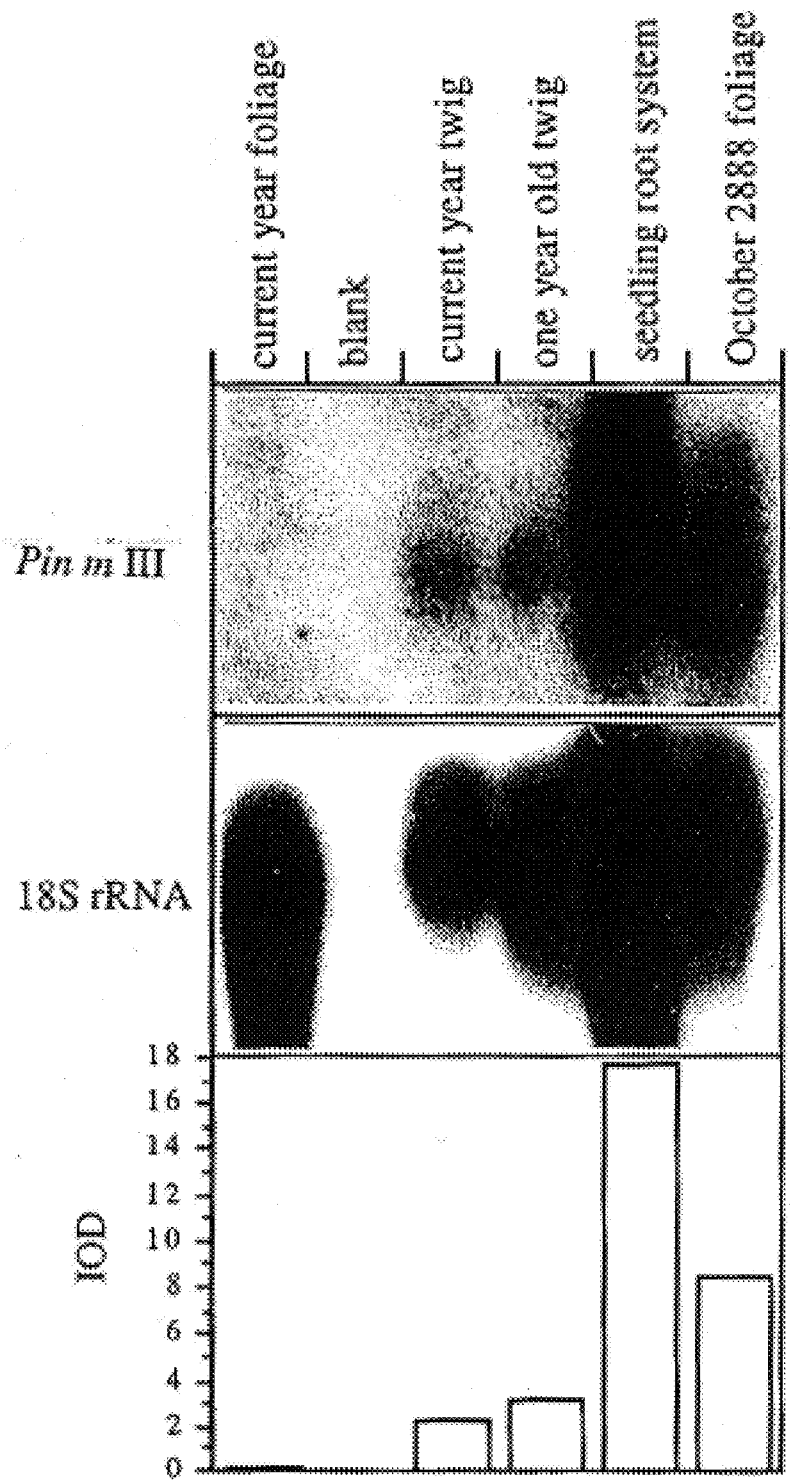
FIG. 6 shows RNA gel blot analysis of *Pin m* III transcript levels in white pine seedling tissues. Samples were collected from healthy western white pine seedling (seedlot 3144) in September 1996. Lane 1, current year foliage; lane 2, one year old foliage; lane 3 current year twig; lane 4, one year old twig and lane 5, root system from the seedling.
Figure 7:
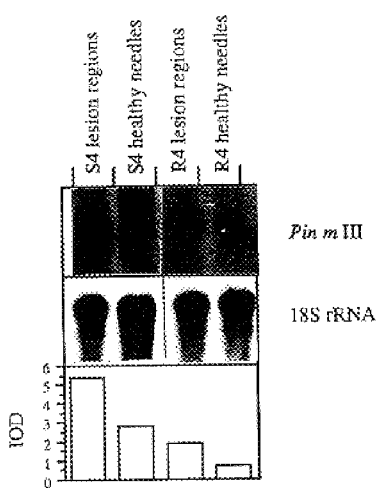
FIG. 7 shows RNA gel blot analysis of *Pin m* III homologue (i.e. *Pin l* I transcript levels in white pine blister fungus infected sugar pine foliage. Lane 1, infected spots of tree R4 (resistant); lane 2, health foliage of tree R4 (resistant) needles; lane 3, infected spots of tree S4 (susceptible) and lane 4, healthy foliage of tree S4 (susceptible).
Figure 8:
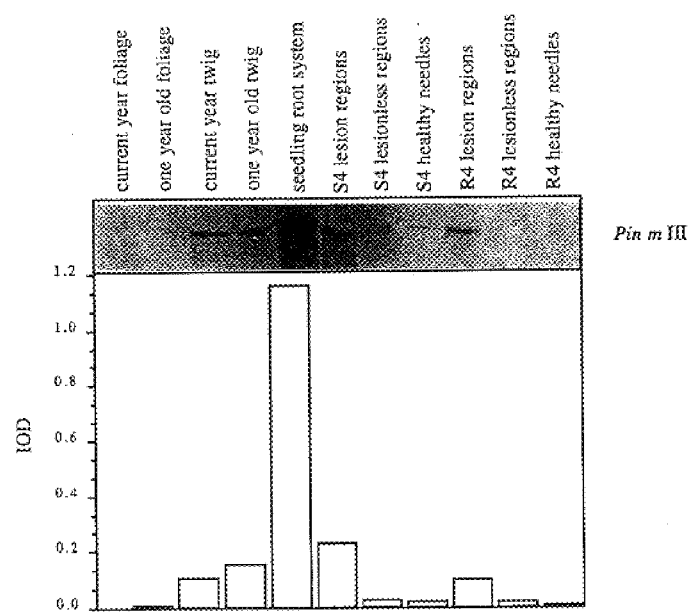
FIG. 8 shows Western immunoblot analysis of *Pin m* III level (lanes 1–5) in different tissues of western white pine from seedlot 3144 collected in September 1996 and *Pin l* I level (lanes 6–11) in sugar pine. Lane 1, current year foliage; lane 2, one year old foliage; lane 3, current year twig; lane 4, one year old twig; lane 5, roots; lane 6, infected spots of tree S4 (susceptible); lane 7, healthy portion of infected foliage of tree S4; lane 8, healthy foliage of tree S4; lane 9, infected spots of tree R4 (resistant); lane 10, healthy portion of infected foliage of seedling R4 and lane 11, health foliage of tree S4.

*Pin m* III is highly expressed in the root although the amount of protein in the foliage or stem is low (FIGS. 6, 7 and FIG. 8).

Presence of the *Pin m* III Homologue Transcripts in the Infected Sugar Pine Needles Western and Northern analysis of blister rust infected resistant and susceptible sugar pine needles showed that both the level of *Pin m* III protein and mRNA are high in the infected needles than the healthy needles (FIGS. 7 and 8). These data would suggest that *Pin m* III is induced by the fungal infection.

Figure 9:
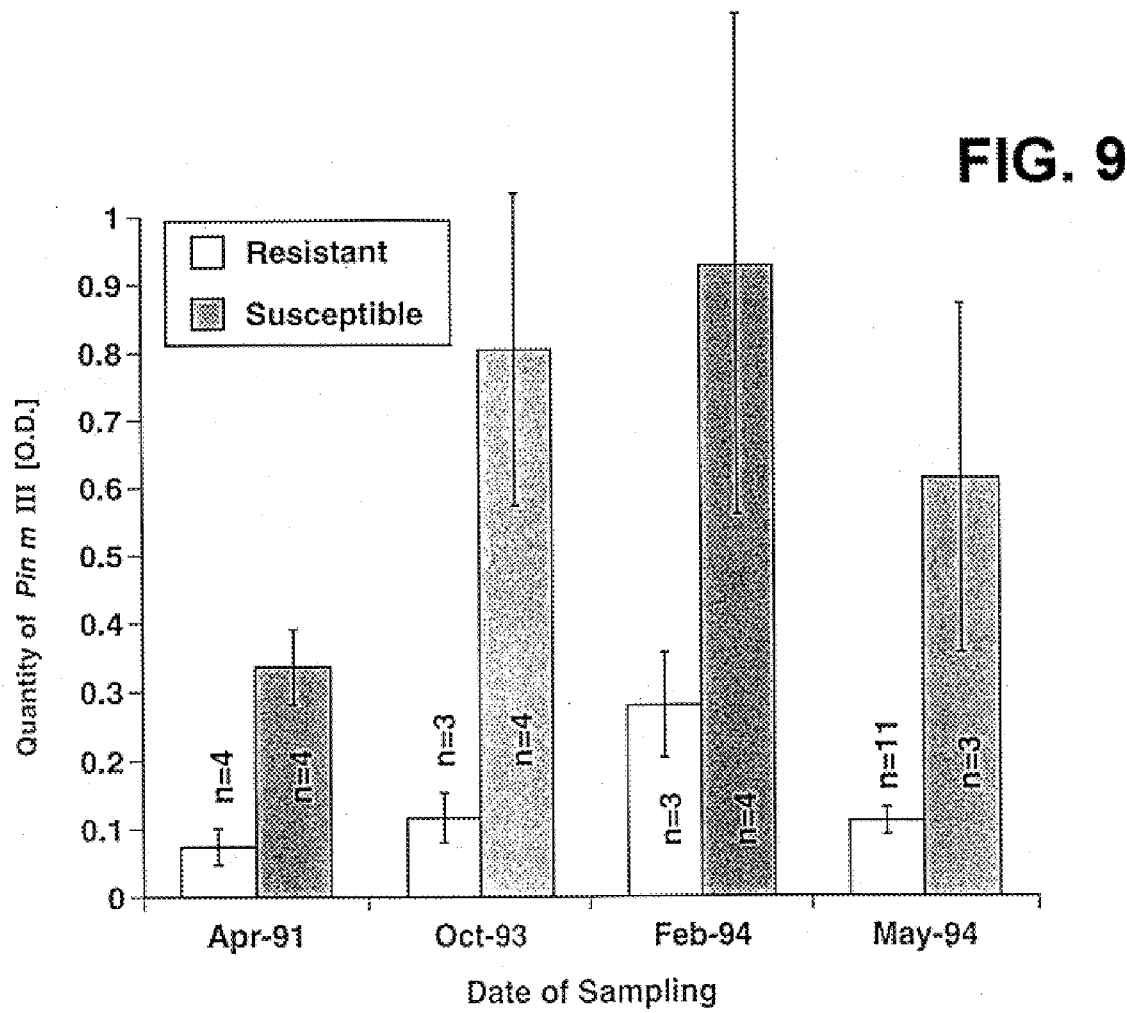
FIG. 9 shows the level of *Pin m* III in the bark samples collected on different dates from mature resistant and susceptible western white pine treees. Error bars represent the standard error of mean quantity of Pin m III in a given number (n) of trees. In case of susceptible trees bark samples were taken from healthy areas away from the cankered tissues. Proteins were separated (5 $\mu$g/lane) by SDS-PAGE followed by Western blot. *Pin m* III was quantified by probing the blot with rabbit anti-*Pin l* I antibody and by scanning the immunoblot.

Identification of *Pin m* III as Pathogenesis-Related Protein Mature Western White Pine The quantity of *Pin m* III in the bark samples that were collected in April 1991 from four resistant and four susceptible white pine trees is shown in FIG. 9. The level of *Pin m* III in susceptible trees was significantly ($p=0.0209$ by Kruskal-Wallis test) higher than that of resistant trees. A similar siginificant difference ($p=0.0339$ by Kruskal-Wallis test )was obtained when these trees were sampled in October 1993 and in February 1994 samples. Eleven ramets representing 4 clones of resistant trees along with three susceptible trees were sampled in May 1994. Again, the level of *Pin m* III in these resistant clone was significantly ($p=0.0102$ by Kruskal-Wallis test) low as compared to susceptible trees.

Western White Pine Seedlings

Cankered bark tissues of all 20 susceptible western white pine seedlings had a significant ($p=05$ by Student-t test) level of *Pin m* III ranging from 0.248 to 2.749 O.D. (see Table I below). This protein was also detected at a much lower level in healthy tissues or tissues outside the canker margin in all these trees. When the marginal and healthy tissues were analyzed by increasing the sample load from 5 to 20 $\mu$g, the level of *Pin m* III was slightly higher with an average of 0.222 for marginal and 0.163 for healthy tissues.

TABLE I

Level of Pin m III (OD) in bark samples of main stem of susceptible western white pine seedlings. Proteins were separated (5 mg/lane) by SDS-PAGE followed by Western blot. Pin m III was quantified by probing the blot with rabbit anti-Pin l I antibody and by scanning the immunoblot

| Seedling number* | Cankered tissue | Outside margin of cankered tissue | Healthy tissue |
| --- | --- | --- | --- |
| 3115B 19-3 | 1.626** | 0.052 | 0.046 |
| 3115B 87-1 | 2.715 | 0.108 | 0.495 |
| 3110 37-1 | 1.96 | 0.032 | 0.467 |
| 3110B 24-2 | 1.884 | 0.04 | 0.029 |
| 3104B 69-2 | 1.604 | 0.023 | 0.026 |
| 3099 56-4 | 1.8 | 0.391 | 0.246 |
| 3111B 16-3 | 1.32 | 0.028 | 0.027 |
| 3111B 34-5 | 0.937 | 0.027 | 0.017 |
| 3099 19-1 | 1.511 | 0.064 | 0.025 |
| 3115B 19-4 | 1.026 | 0.102 | 0.082 |
| 3104B 51-3 | 1.352 | 0.354 | 0.122 |
| 3115B 87-3 | 1.998 | 0.124 | 0.022 |
| 3104B 69-5 | 1.148 | 0.031 | 0.03 |
| 3111B 21-4 | 0.491 | 0.02 | 0.024 |
| 3115B 37-1 | 1.616 | 0.024 | 0.034 |
| 3099 49-4 | 1.019 | 0.07 | 0.058 |
| 3104B 69-1 | 0.829 | 0.693 | 0.174 |
| 3115B 19-1 | 0.248 | 0.012 | 0.019 |
| 3093 16-4 | 0.572 | 0.021 | 0.025 |
| 3110B 129-4 | 2.749 | 0.672 | 0.121 |
| Mean*** | 1.4203$^A$ | 0.1444$^B$ | 0.1044$^B$ |

*first four digits followed by letter or space refer to the seed source (i.e. family) of the seedlings while last three or four digits identifies the individual seedling.
**O.D. units per mm
***means with same letter are not significantly different The level of *Pin m* III in twigs and foliage of these seedlings is shown in Table II.

TABLE II

Level of Pin m III (OD) in twig and foliar samples of susceptible western white pine seedlings. Proteins were separated (20 $\mu$g/lane) by SDS-PAGE followed by Western blot. Pin m III was quantified by probing the blot with rabbit anti-Pin l I antibody and by scanning the immunoblot

| Seedling number* | Current year twig | 1-year old twig | 2-year old twig | foliage of Current year twig | foliage of 1-year old twig | foliage of 2-year old twig |
| --- | --- | --- | --- | --- | --- | --- |
| 3115B19-3 | 0** | 0 | 2.389 | 0 | 0 | 0 |
| 3115B87-1 | 0.058 | 0.675 | 3.369 | 0 | 0.036 | 0.023 |
| 311037-1 | 0 | 0 | 0 | 0 | 0.025 | 0.028 |
| 3110B24-2 | 0 | 0 | 1.545 | 0 | 0.019 | 0.033 |
| 3104B69-2 | 0 | 0 | 3.63 | 0 | 0 | 0 |
| 309956-4 | 0 | 0 | 2.821 | 0 | 0 | 0 |
| 3111B16-3 | 0 | 0 | 0 | 0 | 0 | 0 |
| 3111B34-5 | 0 | 0 | 0.164 | 0 | 0 | 0.093 |
| 309919-1 | 0 | 0 | 0.055 | 0 | 0 | 0 |
| 3115B19-4 | 0 | 0 | 0.802 | 0 | 0 | 0 |
| 3104B51-3 | 0 | 0 | 1.5 | 0 | 0.096 | 0.07 |
| 3115B87-3 | 0 | 0 | 0 | 0 | 0 | 0 |
| 3104B69-5 | 0 | 0 | 0.47 | 0 | 0 | 0 |
| 3111B21-4 | 0 | 0 | 0 | 0 | 0 | 0 |
| 3115B37-1 | 0 | 0 | 0.049 | 0 | 0 | 0 |
| 309949-4 | 0 | 0 | 0 | 0 | 0 | 0 |
| 3104B69-1 | 0 | 0 | 0.437 | 0 | 0 | 0 |
| 3115B19-1 | 0 | 0.042 | 0 | 0 | 0 | 0 |
| 309316-4 | 0 | 0 | 0 | 0 | 0 | 0 |
| 3110B129-4 | 0 | 0.212 | 0.263 | 0 | 0 | 0 |
| Mean*** | 0.0029$^B$ | 0.0465$^B$ | 0.8775$^A$ | 0$^B$ | 0.0088$^B$ | 0.0123$^B$ |

*first four digits followed by letter or space refer to the seed source (i.e, family of the seedlings while last three or four digits identifies the indivdual seedling.
**O.D. units per mm
***means with same letter are not significantly different These twigs or foliage were devoid of cankers or infection spots during the sampling time. The samples were analyzed at 20 $\mu$g protein load per lane. In current year twigs, only one tree had detectable level of Pin m III. In 1-year old twig, three trees had detectable level of *Pin m* III. In 2-year old twigs thirteen trees had detectable level of *Pin m* III. None of the foliar samples of current year twig had any detectable level of *Pin m* III. A low level of *Pin m* III could be detected in the foliage of four 1-year old twigs and five 2-year-old twigs. Comparative anlysis of the mean values showed that 2-year old twigs had significant ($p=0.05$ by Student-t test) of *Pin m* III than that of other tissues.

Table III shows the level of *Pin m* III in twigs and foliage of western white pine seedlings exhibiting a slow canker growth resistant in their stems. The stem bark of these trees were not sampled, because this would have destroyed the trees which were saved for seed orchards propagation. *Pin m* III was detectable in the current year twig of one tree, and in the 1-year old twig of six trees and in the 2-year old twig of eight trees. None of these trees had any detectable level of *Pin m* III in the foliage of current year twig. *Pin m* III was detectable in the foliage of one-year old twig of three trees, and in the foliage of 2-year old twig of eight trees.

TABLE III

Level of Pin m III (OD) in twig and foliar samples of resistant (slow canker growth) western white pine seedlings. Proteins were separated (20 μg/lane) by SDS-PAGE followed by Western blot. Pin m III was quantified by probing the blot with rabbit anti-Pin l I antibody and by scanning the immunoblot

| Seedling number* | Current year twig | 1-year old twig | 2-year old twig | foliage of current year twig | foliage of 1-year old twig | foliage of 2-year old twig |
|---|---|---|---|---|---|---|
| 3110B1-2 | 0** | 0 | 0 | 0 | 0 | 0 |
| 3115B32-4 | 0 | 0 | 0 | 0 | 0 | 0 |
| 3110B76-5 | 0 | 0 | 0 | 0 | 0 | 0.026 |
| 3110B3-4 | 0 | 0 | 0.075 | 0 | 0 | 0 |
| 3104B117-2 | 0 | 0.051 | 0.487 | 0 | 0 | 0.026 |
| 309949-3 | 0 | 0 | 0.051 | 0 | 0.219 | 0 |
| 31111B120-2 | 0 | 0 | 0.057 | 0 | 0 | 0 |
| 3111B4-3 | 0 | 0 | 0 | 0 | 0 | 0 |
| 309940-5 | 0 | 0 | 0 | 0 | 0.022 | 0.03 |
| 3111B62-2 | 0 | 0 | 0 | 0 | 0 | 0 |
| 3111B58-4 | 0 | 0 | 0 | 0 | 0 | 0 |
| 3115B13-2 | 0 | 0 | 0 | 0 | 0 | 0 |
| 3104B6-1 | 0 | 0.053 | 0 | 0 | 0 | 0.024 |
| 3111B54-2 | 0 | 0 | 0.205 | 0 | 0 | 0 |
| 311594-4 | 0.492 | 0 | 0 | 0 | 0 | 0 |
| 3111B16-5 | 0 | 0 | 0 | 0 | 0 | 0 |
| 3104B51-4 | 0 | 0 | 0 | 0 | 0.05 | 0.042 |
| 309316-1 | 0 | 0 | 0.345 | 0 | 0 | 0 |
| 3110B13-5 | 0 | 0.142 | 0.399 | 0 | 0 | 0.026 |
| 3117B31-1 | 0 | 0.044 | 0 | 0 | 0 | 0.238 |
| 309326-4 | 0 | 0.501 | 0 | 0 | 0 | 0.146 |
| 309341-3 | 0 | 0 | 0.529 | 0 | 0 | 0 |
| 3115B94-4 | 0 | 0.618 | 0 | 0 | 0 | 0 |
| Mean*** | $0.022^B$ | $0.061^B$ | $0.0934^B$ | 0 | $0.0127^B$ | $0.0240^B$ |

*first four digits followed by letter or space refer to the seed source (i.e., family) of the seedlings while last three or four digits identifies the individual seedling.
**O.D. units per mm
*** means with same letter are not significantly different

Discussion

During our investigations of the molecular analysis of the host pathogen interaction of the white pine blister rust pathosystem (Ekramoddoullah and Hunt, 1993, Ref. 10), a sugar pine protein, Pin l I, was detected in increasing amounts in the fall (Ekramoddoullah et al., 1995, Ref. 12). Using anti-Pin l I antibody, its homologue Pin m III was detected in western white pine. Furthermore, the concentration of Pin m III, which reached its maximum in winter months, was significantly correlated with frost hardiness of western white pine foliage. In order to study the potential anti-freeze property of Pin m III, we constructed an expression cDNA library. Sequence analysis revealed similarity between the predicted Pin m III polypeptide and the asparagus AoPR1, the bean PvPR1 and PvPR2 proteins, the potato pSTH2 protein, the pea PI49 protein, the parsley PcPR1-1 protein and a major pollen allergen from birch (Bet v I). These transcripts have been shown to be induced in response to pathogen attack.

The IPRs are subgrouped while the allergens formed the other subgroups suggesting a divergence of functions inherent to the subgroups. Pin m III is most related to the PR1 from asparagus suggesting its closeness to monocotyledons.

Both Pin m III and Bet v 1 belong to a class of intracellular PR proteins, as revealed by sequences in the protein databases. These proteins are known to be strongly up-regulated in plants by pathogens or by treatment of cell cultures with microbial elicitors. These proteins are present in di-cotyledons, monocotyledons, and in conifers from various taxonomically distantly related plant families. In particular, the deduced amino acid sequence of Pin m III showed a striking similarity to the asparagus PR protein. In parsley, in situ RNA hybridization in fungus-infected parsley leaf tissue demonstrated rapid and massive PR mRNA accumulation around infection sites. These findings are considered to indicate a close correlation between PR mRNA accumulation and the disease-resistance response of the plant and the restriction of fungal growth.

Level of Pin m III in the infected white pine trees confirms the PR nature of Pin m III. Thus repeated sampling over 3 years demonstrated that the quantity of Pin m III in the bark of mature trees was high in susceptible trees during summer. Because the content of Pin m III accumulates in winter months and then decreases in summer months (Ekramoddoullah et al., 1995, Ref. 12), this result would suggest that the high level of Pin m III observed in late spring samples was due to continued presence of the blister rust fungus.

To corroborate this finding further in a larger number trees, we analyzed the quantity of Pin m III in forty three 7-year-old white pine seedlings which were previously inoculated with blister rust fungus as a part of ongoing screening program. Seedlings were selected based on slow canker growth (a form of resistance) vs normal canker growth in their stems. Seedlings from the same families were represented in both groups. Because the difference in the quantity of Pin m III between resistant and susceptible mature trees was found to be more in late spring/early summer samples, sampling in these seedlings was done in summer. The results clearly showed that the content of Pin m III in cankered tissues was highest in susceptible trees indicating that host's cell which are in immediate contact with fungus are capable of producing Pin m III. Consistent with this observation it was found that Pin m III could be detected only in spots of infected needles collected in summer months. Since the cankered tissues of slow canker growth trees could not be analyzed without destroying these trees, we decided to analyze the level of Pin m III in twigs and foliage of both susceptible and slow canker growth seedlings. In general, the quantity of Pin m III was higher in 2-year old twigs than foliage of all seedlings tested. However, a greater percentage of susceptible trees had detectable levels of Pin m III than that of slow canker-growth trees in their 2 year-old twigs (cf Tables II & III). This difference is highly significant by Kruskal-Wallis test (p=0.0179).

The findings that Pin m III which normally accumulates in winter months can also be induced by the fungus is similar to some pathogenesis-related proteins that are induced by both biotic and abiotic stress (Lin et al., 1996, Ref. 24). It is possible that there is a common denominator that perceives signals by two different stresses. For example, in overwintering plants which have to survive frost, limiting water potential could be a factor for its survival. It has been suggested that microbial colonization of plants is also restricted by regulating water potential by the host (Pearce, 1996, Ref. 33). Overwintering grasses that have to survive freezing temperature and desiccation are known to be more resistant to fungal diseases (Tronsmo, 1984, 1985, Refs. 45 and 46; Tronsmo et al., 1993, Ref. 47). Based on the genotypic correlation between freezing tolerance and resistance to the snow molds Typhula ishikariensis and Fusanium nivale (Tronsmo et al, 1993, Ref. 47), it was suggested (Hon et al., 1995, Ref. 18) that the same genetic trait(s) may be involved in both disease and freezing tolerance. There is no evidence at this point that Pin m III provides any protection against the fungal infection; however, sequence similarity with known PR proteins e.g. disease resistance response gene in garden pea and since the expression of a large number pathogenesis-related proteins is temporal and spatial particularly in infection sites would suggest a defensive role of *Pin m* III in white pine blister rust pathosystem.

References

1. Altschul S F, Gish W, Miller W, Myers E W, Lipman D J (1990) Basic local alignment search tools. J Mol Biol 215: 403–410).
2. Atkinson R G, Perry J, Matsui T, Ross G S, Macrae E A: (1996) A stress-pathogenesis-, and allergen-related cDNA in apple fruit is also ripening-related. New Zealand J Crop Horti Sci: 24: 103–107.
3. Bohnert H J, Nelsen D E, Jensen R G (1995) Adaptations to enviromental stresses. The Plant Cell 7: 1099–1111.
4. Breiteneder H, Pettenburger K, Bito A, Valenta R, Kraft D, Rumpold H, Scheiner O, Breitenbach M: (1989) The gene coding for the major birch pollen allergen Betv1, is highly homologous to a pea disease resistance response gene. EMBO J 8: 1935–8.
5. Clausen S, Apel K (1991) Seasonal changes in the concentration of major storage protein and its mRNA in xylem ray cells of poplar trees. Plant Mol Biol 17: 669–678.
6. Davidson J J, Ekramoddoullah, A K M (1997) Analysis of bark proteins in blister rust-resistant and susceptible western white pine (*Pinus monticola*). Tree Physiology (17:663–669).
7. Davis J M, Egelkrout E E, Coleman G D, Chen T H H, Haissig, B E, Reimenscheider D E, Gordon M P (1993) A family of wound induced genes in Populas shares common features with genes encoding vegetative storage proteins. Plant Mol Biol 23: 135–143.
8. Ekramoddoullah A K M (1991) Analysis of proteins of western white pine (*Pinus monticola* Dougl.) needles. In Rusts of Pine. Proc. 3rd IUFRO Rusts of Pine Working Party Conference, Sept. 18–22, 1989, Banff, Alberta. Edited by Hiratsuka, Y., Samoil, J. K., Blenis, P. V., Crane, P. E., and Laishley, B. L. pp. 102–108, For. Can, Northwest Reg., North. For. Cent., Edmonton, Alberta. Inf. Rep. Nor-X-317.
9. Ekramoddoullah A K M (1993) Analysis of needle proteins and N-terminal amino acid sequence of two photosystem II proteins of western white pine (*Pinus monticola* D. Don). Tree Physiol. 12: 101–106.
10. Ekramoddoullah A K M, Hunt R S (1993) Changes in protein profile of susceptible and resistant sugar pine foliage infected with white pine blister rust fungus, *Cronartium ribicola*. Can. J. Plant Pathol. 15: 259–264.
11. Ekramoddoullah A K M, Davidson J J. (1995) A method for the determination of conifer foliage protein extracted using sodium dodecyl sulfate and mercaptoethanol. Phytochemical Analysis. 6: 20–24.
12. Ekramoddoullah A K M, Taylor D W, Hawkins B J (1995) Characterization of a fall protein and detection of its homologues associated with frost hardiness of western white pine needles. Can. J. For. Res. 25: 1137–1147.
13. Ekramoddoullah A K M, Taylor D W (1996) Seasonal variation of western white pine (*Pinus monticola* D. Don) foliage proteins. Plant Cell Physiol. 37: 189–199.
14. Felsenstein J: PHYLIP (1989) Phylogeny Interference Package (Version 3.2). Cladistics 5: 64–166.
15. Gajhede M, Osmark P, Poulsen F M, Ipsen H, Larsen J N, Joost van Neerven R J, Schou C, Lowenstein H, Spangfort M D: (1996) X-ray and NMR structure of *Bet v* I, the origin of birch pollen allergy. Nat. Struct. Biol. 3: 1040–1045.
16. Heikila J J, Papp J E T, Schutz G A, Bewley J D (1984) Induction of heat shock messenger RNA in maize mesocotyls by water stress, absasic acid, and wounding. Plant Physiol. 76: 207–274.
17. Hightower L E (1991) Heat shock, stress proteins, chaperons, and phytotoxicity. Cell 66: 191–197.
18. Hon W C, Griffith M, Mlynarz A, Kwok Y C, Yang D S (1995) Antifreeze proteins in winter rye are similar to pathogenesis-related proteins. Plant Physiol 109: 879–889.
19. Hunt R S, Meagher M D, Craig H (1987) White pine plantations in British Columbia. I. Plantations prior to 1975. Forestry Canada, Pacific Forestry Centre file report 54/04 Victoria, British Colombia, Canada.
20. Hunt R S (1988) White pine improvement in British Columbia. Pages 32–36 in RS Hunt, compiler, Proceedings of a western white pine management symposium, Nakusp, British Columbia, May 2–5,1988. Forestry Canada, Pacific forestry Centre, Victoria, B.C. Canada.
21. Hunt R S, Meagher M D (1989) Incidence of blister rust on "resistant" white pine (*Pinus monticola* and *P. strobus*) in coastal British Columbia plantations. Can J. Plant Pathol. 11: 419–423.
22. Hunt R S (1997) Relative value of slow canker growth and bark reactions as resistance mechanisms to white pine blister rust. Can. J. For. Res.(submitted).
23. Laemmli U K (1970) Cleavage of structural proteins during the assembly of the head of bacteriophage T4. Nature 227: 680–685.
24. Lin K-C, Bushnell W R, Szabo L J, Smith A G (1996) Isolation and expression of a host response gene family encoding thaumatin-like proteins in compatible oat-stem rust fungus interactions. Molecular Plant-Microbe Interactions. 9: 511–522.
25. Linthorst H J M (1991) Pathogenesis-related proteins of plants. Crit. Rev. Plant Sci. 10: 123–150.
26. Maeshima M, Sasaki T, Asahi T (1985) Characterization of major proteins in sweet potato tuberous roots. Phytochemistry 24: 1899–1902.
27. Mason H S, Mullet J E (1990) Expression of two soybean vegetative storgae proteins genes during development and in response to water deficit, wounding, and jasmonic acid. Plant Cell 2: 569–579.
28. Mauch F, Mauch-Mani B, Boller T (1988) Antifungal hydrolases in pea tissue. II. Inhibition of fungal growth by combination of chitinase and $\beta$-1,3 glucanase. Plant Physiol. 88: 936–942.
29. Meagher M D, Hunt R S, White E E, Ekramoddoullah, AKM, Jensen G D, Dronzek J (1995) Western white pine improvement program for British Columbia. In Evolution and Tree Breeding. Proc. 25th Canadian Tree Improvement Association, August 28–September 1, Victoria, British Columbia, Editor J. Lavereau. pp 28–32.
30. Misra S (1994) Conifer zygotic embryogenesis, somatic embryogenesis and seed germination: Biochemical and molecular advances. Seed Sci Res 4: 357–384.
31. Ohto M, Nakamura-Kito K, Nakamura K (1992) Induction of expression of genes coding for sporamin and p-amylase by polygalacturonic acid in leaf-petiole cuttings of sweet potato. Plant Physiol 99: 422–427.
32. Ort D R, Mariono S, Wise R R, Kent J, Cooper P (1989) Changes in protein synthesis induced by chilling and their influence on the chilling sensitivity of photosynthesis. Plant Physiol Biochem 27: 785–793.
33. Pearce R B (1996) Antimicrobial defences in the wood of living trees. New Phytol. 132: 203–233.
34. Porter W A (1960) Testing for resistance to the blister rust disease of western white pine in British Columbia.

35. Ragothama K G, Liu D, Nelson D E, Hasegawa P M, Bressan R A (1993) Analysis of an osmotically regulated pathogenesis-related osmotin gene promoter. Plant Mol Biol 23: 1117–1128.
36. SAS Institute Inc. 1989. SAS/STA user's guide, version 6, 4th edition, Cary, NC. 12900 pp.
37. Sabehat A, Weiss D, Lurie S (1996) The correlation between heat shock protein accumulation and persistence and chilling tolerance in tomato fruit. Plant Physiol. 110: 531–537.
38. Sambrook J, Fitsch E F, Maniatis T: (1989) Molecular Cloning: A laboratory manual, 2nd ed. Cold Spring Harbor Press, Cold Spring Harbor, N.Y.
39. Schultz D J, Craig R, Cox-Foster D L, Mumma R O, Medford J I (1994) RNA isolation from recalcitrant plant tissue. Plant Mol Biol Rep 12: 310–316.
40. Stintzi A, Heitz T, Kauffman S, Legrand M, Fritig B (1991) Identification of a basic pathogenesis protein of virus infected tobacco as osmotin. Physiol Mol Plant Pathol. 38:137–146.
41. Stintzi A, Heitz T, Prasad V, Wiedemann-Merdinoglu S, Kauffman S, Geoffroy P, Legrand M, Fritig B (1993) Plant pathogenesis related proteins and their role in defense against pathogens. Biochimie 75: 687–706.
42. Swoboda I, Jilek A, Ferreira F, Engel E, Hoffman-Sommergruber K, Scheiner O, Kraft D, Breiteneder H, Pittenauer E, Schmid E, Vicente O, Heberle-Bors E, Ahorn H, Breitenbach M (1995) Isoforms of Bet v I, the major birch pollen allergen, analyzed by liquid chromatography, mass spectrometry, and cDNA cloning. J Biol Chem 270:2607–2613.
43. Thompson J D, Higgins D G, Gibson T J: CLUSTAL W (1994) Improving the sensitivity of progressive multiple sequence alignment through sequence weighting, positions-specific gap penalties and weight matrix choice. Nucleic Acids Research 22:4673–4680.
44. Towbin H, Stahelin T, Gordon J (1979) Electrophoretic transfer of proteins from polyacrylamide gels to nitrocellulose sheets: procedure and some applications. Proc. Natl. Acad. Sci. USA 76: 4350–4354.
45. Tronsmo A M (1984) Predisposing effects of low temperature on resistance to winter stress factors in grasses. Acta Agric Scand 34: 210–220.
46. Tronsmo A M (1985) Induce resistance to biotic stress factors in grasses by frost hardening. In A. Kaurin, O Juntilla, J Nilsen, eds, Plant Production in the North. Norwegian University Press, Tromso, Norway, pp 127–133.
47. Tronsmo A M, Gregersen P, Hjeljord L, Sandal T, Bryngelsson T, Collinge D B (1993) Cold-induced disease resistance. In B. Fritig, M Legrand, eds, Mechanisms of Plant Defense Responses. Kluwer Academic, The Netherlands, p369.
48. van Loon L C (1985) Pathogenesis related proteins. Plant Mol Biol 4: 111–116.
49. Walter M H, Liu J W, Grand C, Lamb C J, Hess D (1990)Bean pathogenesis-related (PR) proteins deduced from elicitor-induced transcripts are members of a ubiquitous new class of conserved PR proteins including pollen allergens. Mol Gen Genet 222: 353–60.
50. Wang C S, Vodkin L O (1994) Extraction of RNA from tissues containing high levels of procyanidins that bind RNA. Plant Mol Biol Rep 12: 132–145.
51. Warner S A, Scott R, Draper J (1992) Characterization of a wound-induced transcript from the monocot asparagus that shares similarity with a class of intracellular pathogenesis-related (PR) proteins. Plant Mol Biol 19: 555–561.
52. Warner S A, Scott R, Draper J (1993) Isolation of an asparagus intracellular PR gene (AoPR1) wound-responsive promoter by the inverse polymerase chain reaction and its characterization in transgenic tobacco. Plant J 3: 191–201.
53. Warner S A, Gill A, Draper J (1994) The developmental expression of the asparagus intracellular PR protein (AoPR1) gene correlates with sites of phenylpropanoid biosynthesis. Plant J 6: 31–43.

We claim:

1. A nucleic acid sequence encoding the protein *Pin m* III having the amino acid sequence of SEQ ID NO: 1.

2. The isolated protein *Pin m* III comprising the open reading frame, from bases 55 to 537 (amino acids 1–161) of SEQ ID NO: 1.

3. A method of determining the frost hardiness of a conifer seedling comprising detecting the amount of a protein having the open reading frame, from bases 55 to 537 (amino acids 1–161) of SEQ ID NO: 1.

4. A method of detecting the presence of blister rust fungus in a conifer comprising measuring the amount of a protein having the open reading frame, from bases 55 to 537 (amino acids 1–161) of SEQ ID NO: 1.

* * * * *